US011026563B2

(12) United States Patent
Ando et al.

(10) Patent No.: US 11,026,563 B2
(45) Date of Patent: Jun. 8, 2021

(54) ENDOSCOPE AND METHOD OF ASSEMBLING ENDOSCOPE

(71) Applicant: FUJIFILM Corporation, Tokyo (JP)

(72) Inventors: Tadashi Ando, Kanagawa (JP); Shozo Iyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 814 days.

(21) Appl. No.: 15/684,946

(22) Filed: Aug. 24, 2017

(65) Prior Publication Data
US 2018/0055334 A1 Mar. 1, 2018

(30) Foreign Application Priority Data

Aug. 29, 2016 (JP) ............................. JP2016-166767

(51) Int. Cl.
*A61B 1/00* (2006.01)
*A61B 1/018* (2006.01)
*A61B 1/24* (2006.01)

(52) U.S. Cl.
CPC .......... *A61B 1/0008* (2013.01); *A61B 1/0011* (2013.01); *A61B 1/00071* (2013.01);
(Continued)

(58) Field of Classification Search
CPC . A61B 1/0008; A61B 1/00096; A61B 1/0011; A61B 1/00105; A61B 1/00112; A61B 1/012; A61B 1/018; A61B 1/04; A61B 1/06; A61B 1/00101; A61B 1/05; A61B 1/053; A61B 1/055; A61B 1/0676;
(Continued)

(56) References Cited

U.S. PATENT DOCUMENTS 4,569,334 A 2/1986 Ohshiro
6,447,445 B1* 9/2002 Hirano ................ A61B 1/0008
600/129

(Continued)

FOREIGN PATENT DOCUMENTS

JP H11-056756 3/1999
JP 2004-290492 10/2004
(Continued)

OTHER PUBLICATIONS

"Search Report of European Counterpart Application", dated Jan. 5, 2018, p. 1-p. 5, in which the listed references were cited.

*Primary Examiner* — Ryan N Henderson
*Assistant Examiner* — Pamela F Wu
(74) *Attorney, Agent, or Firm* — JCIPRNET

(57) ABSTRACT

According to an aspect of the invention, the circumferential position of a protrusion portion of a light guide member is aligned with the position of a second groove portion of a pressing member and a tip portion of the light guide member is inserted into an insertion hole. Next, the light guide member is rotated to align the circumferential position of the protrusion portion of the light guide member with the position of a first groove portion of a mounting hole, and the tip portion of the light guide member is mounted in the mounting hole of a tip portion body. After that, a screw member is inserted into a through hole of the pressing member, is threadedly inserted into a screw hole of the tip portion body, and fixes the pressing member to a base end face of the tip portion body.

10 Claims, 14 Drawing Sheets

(52) U.S. Cl.
CPC .......... *A61B 1/00112* (2013.01); *A61B 1/018* (2013.01); *A61B 1/24* (2013.01)

(58) Field of Classification Search
CPC .............. A61B 1/0669; A61B 1/00071; A61B 1/00073; A61B 1/00091; A61B 1/00188; A61B 1/0019; A61B 1/00197; A61B 1/002; A61B 1/025; A61B 1/00087; A61B 1/00098
USPC .................................................. 600/129, 109
See application file for complete search history.

(56) References Cited

U.S. PATENT DOCUMENTS

| | | | |
|---|---|---|---|
| 8,864,653 B2 | 10/2014 | St Onge et al. | |
| 2012/0149979 A1 | 6/2012 | Mitelberg | |
| 2012/0150200 A1 | 6/2012 | Mitelberg | |
| 2012/0157765 A1 | 6/2012 | Mitelberg | |
| 2012/0232343 A1* | 9/2012 | Levy .................... | A61B 1/0684 600/109 |
| 2014/0330081 A1* | 11/2014 | Imai .................. | A61B 1/00163 600/129 |
| 2016/0045197 A1 | 2/2016 | Mitelberg et al. | |

FOREIGN PATENT DOCUMENTS

| | | |
|---|---|---|
| JP | 2014519880 | 8/2014 |
| WO | 2015150078 | 10/2015 |

\* cited by examiner

ENDOSCOPE AND METHOD OF ASSEMBLING ENDOSCOPE

CROSS-REFERENCE TO RELATED APPLICATIONS

The present application claims priority under 35 U.S.C. § 119 to Japanese Patent Application No. 2016-166767, filed on Aug. 29, 2016. The above application is hereby expressly incorporated by reference, in its entirety, into the present application.

BACKGROUND OF THE INVENTION

1. Field of the Invention

The present invention relates to an endoscope, and more particularly, to an endoscope of which a tip portion of an insertion member is fixed to a tip portion body of a hard tip part provided at a tip of an insertion unit and a method of assembling the endoscope.

2. Description of the Related Art

An insertion unit of an endoscope includes a soft part, a bendable part, and a hard tip part that are arranged from a base end portion thereof toward a tip portion thereof and are connected. Further, insertion members, such as a light guide member, an air/water supply tube member, a forceps tube member, an image guide member, and a signal cable member, are disposed so as to be inserted into the insertion unit, and tip portions of these insertion members are fixed to a tip portion body of the hard tip part.

For example, a tip mouthpiece or a pipe is fixed to the tip portion of each of the light guide member, the forceps tube member, and the air/water supply tube member, and the tip mouthpieces or the pipes are inserted and fixed to mounting holes formed in the tip portion body. Further, a lens barrel, which holds an optical system, is connected to the tip portion of the image guide member, an imaging device to which the lens barrel holding the optical system is connected is connected to the tip portion of the signal cable member, and the lens barrel is inserted and fixed to the mounting hole of the tip portion body. In this specification, the tip mouthpiece, the pipe, and the lens barrel are generally referred to as a mouthpiece.

JP1999-56756A (JP-H11-56756A) and JP2004-290492A disclose endoscopes of which a fixing structure and an assembling method fixing tip portions of insertion members to a tip portion body.

The endoscope of JP1999-56756A (JP-H11-56756A) includes a tip portion body that includes insertion holes in which an air/water supply nozzle unit and an objective observation unit are disposed and screw holes passing through the tip portion body from the outer peripheral surface of the tip portion body so as to communicate with the insertion holes. According to a method of assembling the endoscope of JP1999-56756A (JP-H11-56756A), the air/water supply nozzle unit and the objective observation unit are disposed in the insertion holes of the tip portion body, fixing screws are threadedly inserted into the screw holes from the outer peripheral surface of the tip portion body, and tip portions of the fixing screws are pressed against the outer peripheral surfaces of the air/water supply nozzle unit and the objective observation unit. The air/water supply nozzle unit and the objective observation unit are fixed to the tip portion body through this procedure.

Further, the endoscope of JP2004-290492A includes a hard tip body that includes insertion holes in which a lens barrel, a support tube, a forceps tube, and an air/water supply tube are disposed and screw holes passing through the hard tip body from the outer peripheral surface of the hard tip body so as to communicate with the insertion holes. According to a method of assembling the endoscope of JP2004-290492A, the lens barrel, the support tube, the forceps tube, and the air/water supply tube are disposed in the respective insertion holes of the hard tip body, and setscrews are threadedly inserted into the screw holes to fix the lens barrel, the support tube, the forceps tube, and the air/water supply tube to the hard tip body.

SUMMARY OF THE INVENTION

However, the endoscopes of JP1999-56756A (JP-H11-56756A) and JP2004-290492A should ensure the number of screw holes or screw threads of the screw holes with which the screws are threadedly engaged sufficiently so that the tip portions of the insertion members are fixed to the tip portion body or the hard tip body. For this reason, the endoscopes have a problem that the outer diameter of the tip portion body or the hard tip body is increased. That is, since there is no margin in the tip portion body except for the regions of the insertion holes in which the insertion members are disposed in a case in which the diameter of the insertion unit is reduced in the endoscopes of JP1999-56756A (JP-H11-56756A) and JP2004-290492A, the screw holes cannot be formed in the tip portion body. Accordingly, the endoscopes of JP1999-56756A (JP-H11-56756A) and JP2004-290492A have a problem that the tip portions of the insertion members cannot be fixed to the tip portion body as long as the diameter of the insertion unit is not increased.

The invention has been made in consideration of the above-mentioned circumstances, and an object of the invention is to provide an endoscope of which a tip portion of an insertion member can be fixed to a tip portion body without an increase in the diameter of an insertion unit and a method of assembling the endoscope.

In order to achieve the object of the invention, an endoscope according to the invention comprises: an insertion unit that has a longitudinal axis; an insertion member that is disposed so as to be inserted into the insertion unit along the longitudinal axis of the insertion unit; a tip portion body that is provided close to a tip of the insertion unit and has a central axis parallel to the longitudinal axis of the insertion unit; a pressing member that is in contact with a base end side of the tip portion body; a protrusion portion that is provided on a tip portion of the insertion member and protrudes outward from an outer periphery of the tip portion of the insertion member in a radial direction; a mounting hole which is provided in the tip portion body and in which the tip portion of the insertion member is inserted and mounted and a first groove portion having a shape corresponding to the protrusion portion is formed and is disposed at a first circumferential position in a circumferential direction around an axial direction of the insertion member; and an insertion hole which is provided in the pressing member, into which the tip portion of the insertion member is inserted, and in which a second groove portion having a shape corresponding to the protrusion portion is formed and is disposed at a second circumferential position different from the first circumferential position in the circumferential direction around the axial direction of the insertion member.

According to the invention, since the circumferential position of the first groove portion of the mounting hole formed in the tip portion body is different from the circumferential position of the second groove portion of the insertion hole formed in the pressing member, the tip portion of the insertion member is fixed to the tip portion body in a state in which the movement of the insertion member to the base end side in the axial direction is restricted. Accordingly, according to the invention, the tip portion of the insertion member can be fixed to the tip portion body without an increase in the diameter of the insertion unit.

According to an aspect of the invention, it is preferable that the endoscope further includes a screw hole provided on a base end face of the tip portion body, a screw insertion hole provided in the pressing member, and a screw member inserted into the screw insertion hole and threadedly inserted into the screw hole.

According to this aspect, the pressing member can be detachably fixed to the base end side of the tip portion body by the screw member. Accordingly, since the pressing member can be easily detached from the tip portion body, it is easy to repair and replace the insertion member.

According to an aspect of the invention, it is preferable that the endoscope further includes a mouthpiece mounted on the tip portion of the insertion member and the protrusion portion is provided on the mouthpiece.

According to this aspect, since the protrusion portion is provided on the mouthpiece, the protrusion portion can be easily disposed at the tip portion of the insertion member.

According to an aspect of the invention, the endoscope preferably further includes: a plate-like cap body that includes a base end face facing a tip surface of the tip portion body and being in contact with the tip surface; a mounting portion including a mounting surface that is a part, which is formed in a planar shape or a concave shape, of an outer peripheral surface of the tip portion body; a cap body-side extending portion that extends toward the tip portion body from the base end face of the cap body and includes an outer surface and a contact surface provided closer to the central axis than the outer surface and being in contact with the mounting surface; a connecting portion that includes a first engagement portion formed on the mounting surface and a second engagement portion formed on the contact surface and connects the cap body to the tip portion body through engagement between the first and second engagement portions; a first recessed fitting portion that is formed along the central axis on the outer surface of the cap body-side extending portion; a second recessed fitting portion that is formed along the central axis on the outer peripheral surface of the tip portion body and is connected to the first recessed fitting portion; and a pressing member-side extending portion that is provided on a tip surface of the pressing member and is engaged with the first recessed fitting portion and the second recessed fitting portion.

According to this aspect, it is possible to fix the pressing member to the base end side of the tip portion body by fitting the pressing member-side extending portion of the pressing member into the first recessed fitting portion of the cap body-side extending portion and the second recessed fitting portion of the tip portion body.

According to an aspect of the invention, it is preferable that the first engagement portion is a first recessed portion and the second engagement portion is a first protruding portion.

According to this aspect, it is possible to prevent the cap body from falling out of the tip portion body while maintaining the strength of the cap body-side extending portion.

According to an aspect of the invention, the endoscope preferably further includes: a coating member that covers the outer peripheral surface of the tip portion body, the outer surface of the cap body-side extending portion, and the pressing member-side extending portion in a case in which the cap body and the tip portion body are connected to each other by the connecting portion; and a stringy or belt-like fixing member that is provided on an outer peripheral surface of the coating member, is disposed at a position where the connecting portion is provided in a direction of the central axis, and fixes engagement between the first and second engagement portions.

According to this aspect, since the engagement between the first and second engagement portions can be fixed through the coating member by the fixing member, the separation of the cap body from the tip portion body can be reliably prevented.

According to an aspect of the invention, it is preferable that the endoscope further includes a second recessed portion provided on the second recessed fitting portion and a second protruding portion provided on the pressing member-side extending portion and engaged with the second recessed portion.

According to this aspect, it is possible to prevent the pressing member from falling out of the tip portion body to the base end side while maintaining the strength of the pressing member-side extending portion.

According to an aspect of the invention, it is preferable that the endoscope further includes a third recessed portion provided on the first recessed fitting portion and a third protruding portion provided on the pressing member-side extending portion and engaged with the third recessed portion.

According to this aspect, it is possible to prevent the pressing member from falling out of the tip portion body to the base end side while maintaining the strength of the pressing member-side extending portion.

According to an aspect of the invention, it is preferable that the insertion member is one of a light guide member, a tube member, and an image guide member.

According to this aspect, the tip portion of the light guide member, the tube member, or the image guide member can be fixed to the tip portion body without an increase in the diameter of the insertion unit of the endoscope.

According to an aspect of the invention, it is preferable that a plurality of the mounting holes are provided and the first groove portion of at least one mounting hole of the plurality of mounting holes is formed so that a direction in which the first groove portion protrudes from an inner peripheral surface of the mounting hole is directed to the central axis in a plane orthogonal to the central axis.

According to this aspect, the outer diameter of the tip portion body can be further reduced.

In order to achieve the object of the invention, there is provided a method of assembling an endoscope according to the invention. The endoscope includes an insertion unit that has a longitudinal axis, an insertion member that is disposed so as to be inserted into the insertion unit along the longitudinal axis of the insertion unit, a tip portion body that is provided close to a tip of the insertion unit, a pressing member that is in contact with a base end side of the tip portion body, a protrusion portion that is provided on a tip portion of the insertion member and protrudes outward from an outer periphery of the tip portion of the insertion member in a radial direction, a mounting hole which is provided in the tip portion body and in which the tip portion of the insertion member is inserted and mounted and a first groove portion having a shape corresponding to the protrusion portion is formed and is disposed at a first circumferential position in a circumferential direction around an axial direction of the insertion member, and an insertion hole which is provided in the pressing member, into which the tip portion of the insertion member is inserted, and in which a second groove portion having a shape corresponding to the protrusion portion is formed and is disposed at a second circumferential position different from the first circumferential position in the circumferential direction around the axial direction of the insertion member. The method comprises an insertion step of inserting the tip portion of the insertion member into the insertion hole of the pressing member in a state in which a circumferential position of the protrusion portion and a circumferential position of the second groove portion are aligned with each other, a mounting step of mounting the tip portion of the insertion member in the mounting hole of the tip portion body in a state in which the circumferential position of the protrusion portion and a circumferential position of the first groove portion are aligned with each other after the insertion step, and a fixing step of fixing the pressing member to the tip portion body.

According to the invention, it is possible to fix a tip portion of an insertion member to a tip portion body without an increase in the diameter of an insertion unit of an endoscope.

DESCRIPTION OF THE PREFERRED EMBODIMENTS

Preferred embodiments of an endoscope and a method of assembling an endoscope according to the invention will be described in detail below with reference to accompanying drawings.

Figure 1:
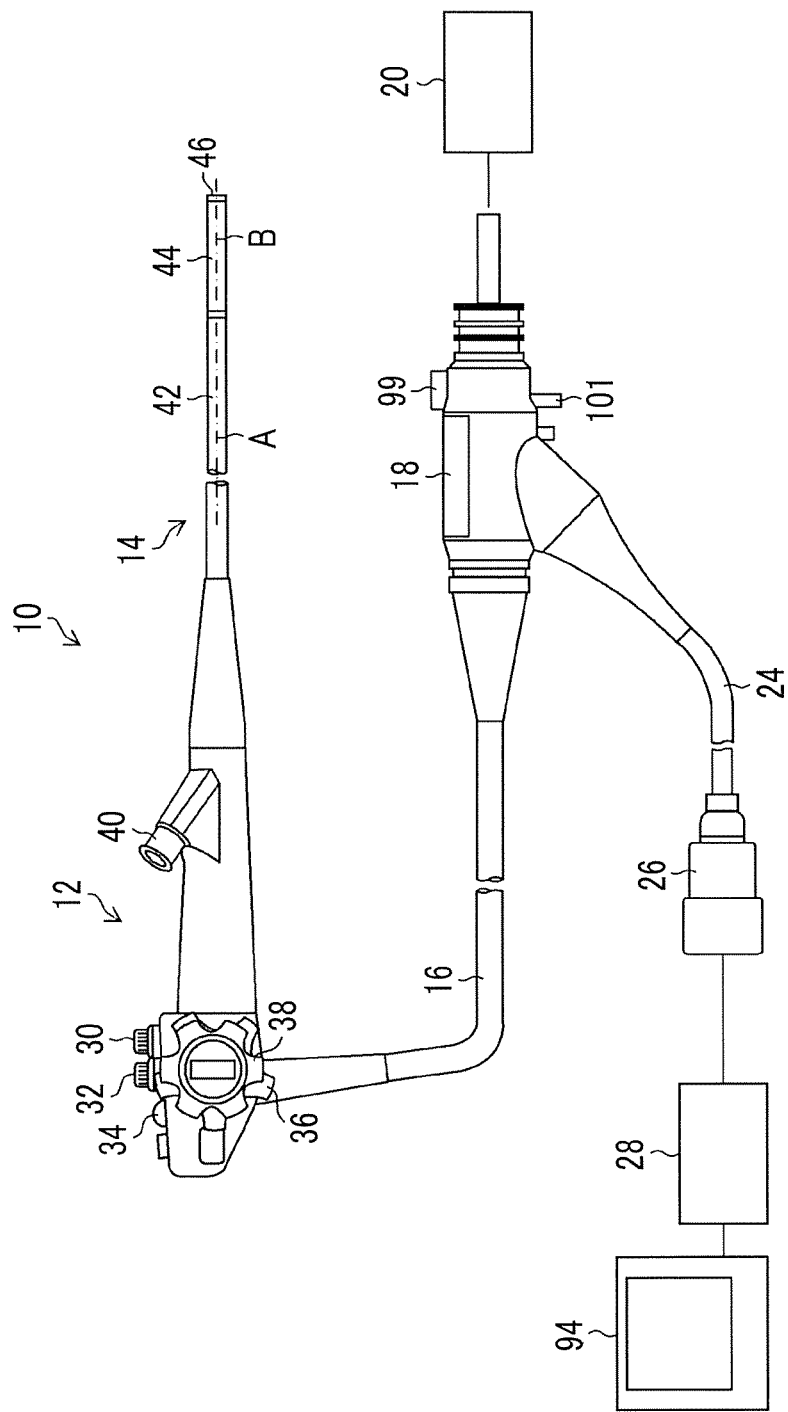
FIG. 1 is a side view showing the entire structure of an endoscope according to an embodiment.

FIG. 1 is a view showing the entire structure of an endoscope 10 of an embodiment.

The endoscope 10 includes an operation unit 12 that is gripped by a practitioner and an insertion unit 14 of which a base end portion is connected to the operation unit 12 and which is to be inserted into a subject. A base end portion of a universal cable 16 is connected to the operation unit 12, and a light guide connector 18 is provided at a tip portion of the universal cable 16. The light guide connector 18 is connected to a light source device 20, so that illumination light is sent to illumination windows 22 and 22 (see FIG. 2) to be described below from the light source device 20. Further, an electrical connector 26 is connected to the light guide connector 18 through a cable 24, and is connected to a processor unit 28.

An air/water supply button 30, a suction button 32, and a shutter button 34, which are to be operated by a practitioner, are provided on the operation unit 12, and a pair of angle knobs 36 and 38 is coaxially and rotatably provided on the operation unit 12. The operation unit 12 is further provided with a forceps insertion portion 40.

The insertion unit 14 includes a soft part 42, a bendable part 44, and a hard tip part 46 that are arranged from the base end portion thereof toward a tip portion thereof and are connected. The bendable part 44 is remotely operated so as to be bent by the rotation of the angle knobs 36 and 38 of the operation unit 12. Accordingly, the hard tip part 46 can be directed in a desired direction.

Figure 2:
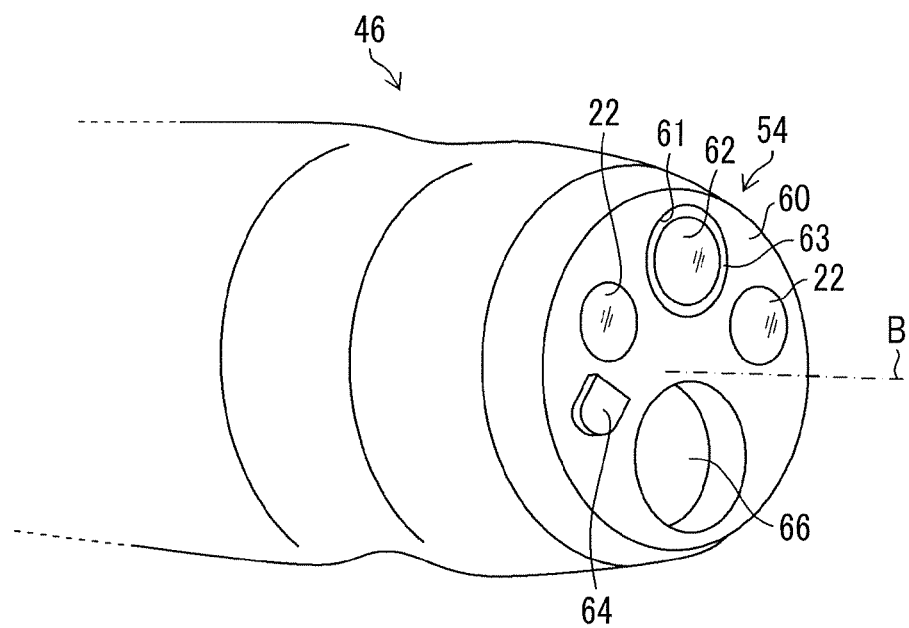
FIG. 2 is a perspective view showing the structure of a tip portion of an insertion unit.
Figure 3:
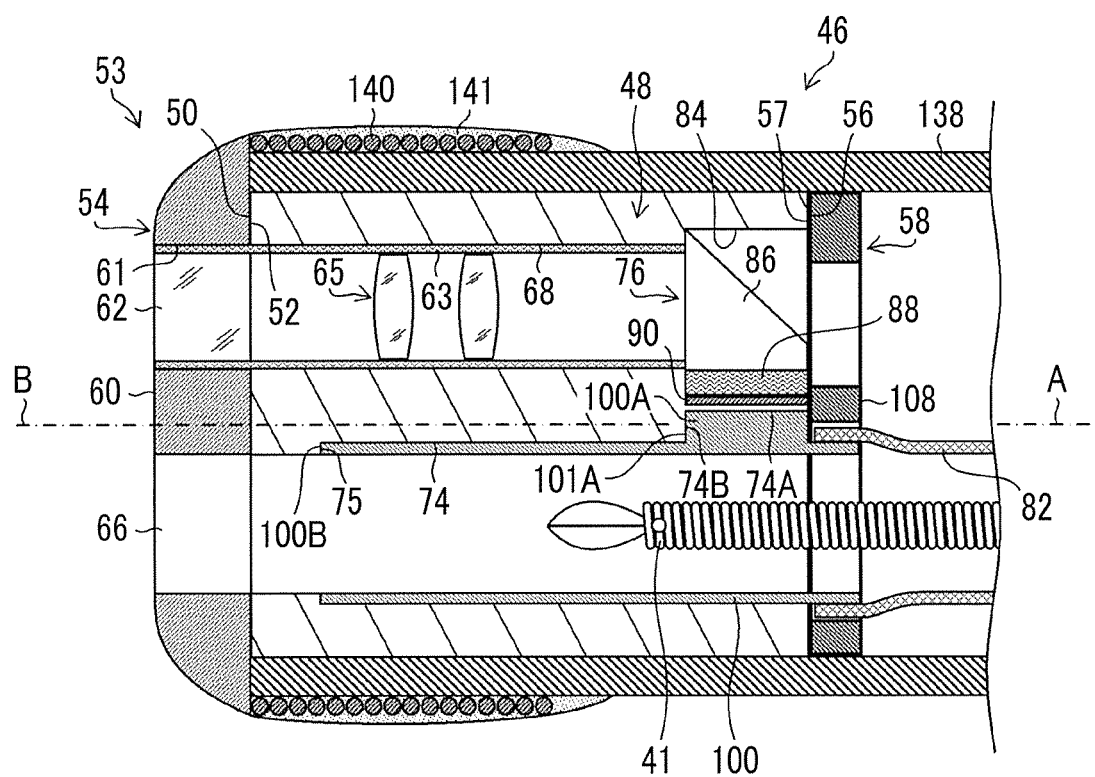
FIG. 3 is a cross-sectional view of a hard tip part taken along a longitudinal axis of the insertion unit.

FIG. 2 is an enlarged perspective view of the main portions of the hard tip part 46. FIG. 3 is a cross-sectional view of the hard tip part 46 and is a cross-sectional view taken along a longitudinal axis A of the insertion unit 14 shown in FIG. 1.

As in FIG. 3, the hard tip part 46 includes a columnar tip portion body 48 that is disposed close to the tip of the insertion unit 14, a cap 53, and a disc-shaped pressing member 58 that includes a tip surface 57 being in contact with a base end face 56 formed on the base end side of the tip portion body 48. The tip portion body 48 is disposed so that a central axis B of the tip portion body 48 is parallel to the longitudinal axis A of the insertion unit 14. That is, the tip portion body 48 has the central axis B parallel to the longitudinal axis A of the insertion unit 14. Further, the cap 53 includes a disc-shaped cap body 54 including a base end face 52 that faces a tip surface 50 of the tip portion body 48 and is in contact with the tip surface 50. Reference numeral 138 of FIG. 3 denotes a coating member that coats the tip portion body 48, reference numeral 140 denotes a fixing member that fixes the tip portion of the coating member 138 to the tip portion body 48, and reference numeral 141 denotes an adhesive that allows the fixing member 140 to adhere to the coating member.

As shown in FIG. 2, a tip surface 60 of the cap body 54 is provided with a through hole 61 in which an observation window 62 is disposed, the above-mentioned illumination windows 22 and 22, an air/water supply nozzle 64, and a forceps port 66.

Figure 4:
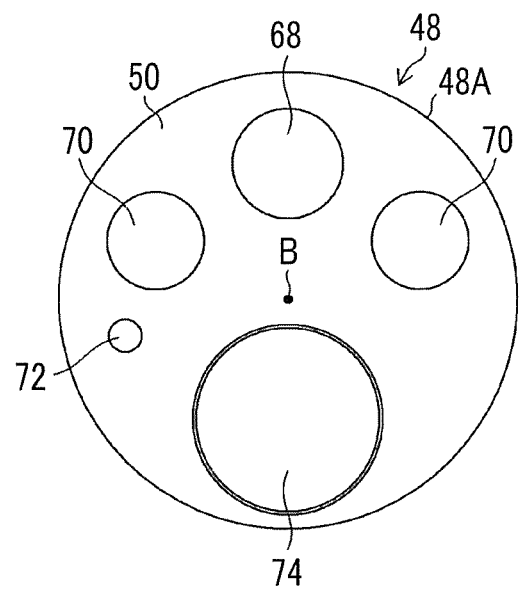
FIG. 4 is a front view of a tip surface of a tip portion body.

FIG. 4 is a front view showing the tip surface 50 of the tip portion body 48.

As shown in FIGS. 3 and 4, the tip portion body 48 is provided with mounting holes 68, 70, 72, and 74 each of which has a circular outer peripheral surface. These mounting holes 68, 70, 72, and 74 are through holes that are provided along the central axis B of the tip portion body 48. The mounting hole 68 is disposed so as to face the through hole 61, and an observation optical system 65, which includes a plurality of lenses held by a lens barrel 63, and an imaging unit 76 are disposed in the mounting hole 68. A tip portion of the lens barrel 63 is fixed to the through hole 61 of the cap body 54, and the observation window 62 is fixed to the tip portion of the lens barrel 63. The mounting holes 70 are disposed so as to face the illumination windows 22 and 22 of FIG. 2, and tip portions 78A of light guide members 78 (see FIG. 7) to be described below, which are insertion members, are inserted into and mounted in the mounting holes 70. The mounting hole 72 of FIG. 4 is disposed so as to face the air/water supply nozzle 64 of FIG. 2, and a tip portion 80A of an air/water supply tube member 80 (see FIG. 7) to be described below, which is an insertion member, is inserted into and mounted in the mounting hole 72. The mounting hole 74 of FIG. 4 is disposed so as to face the forceps port 66 of FIG. 2, and a tip portion 82A of a forceps tube member 82 (see FIG. 7) to be described below, which is an insertion member, is inserted into and mounted in the mounting hole 74.

Figure 5:
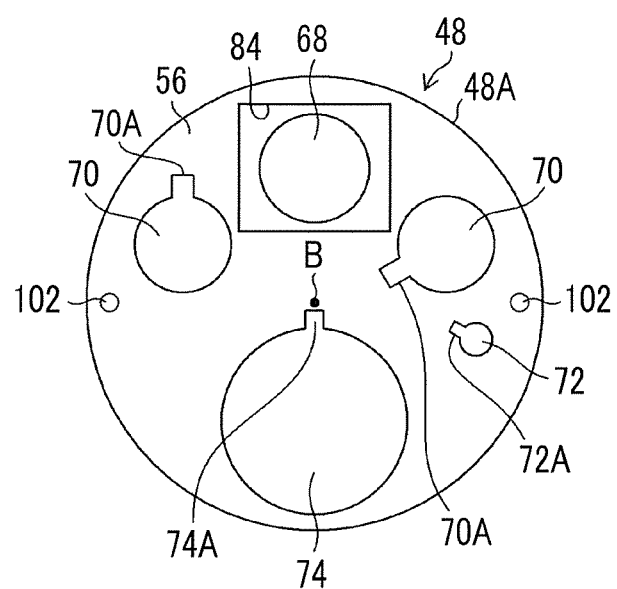
FIG. 5 is a front view of a base end face of the tip portion body.

FIG. 5 is a front view of the base end face 56 of the tip portion body 48.

A rectangular opening portion 84 is connected to the base end side of the mounting hole 68. The imaging unit 76, which includes a prism 86, an imaging element 88, and a substrate 90 supporting the imaging element 88, is disposed so as to be housed in the opening portion 84 as shown in FIG. 3. A tip portion of a signal cable 92 (see FIG. 7) is connected to the substrate 90. A base end portion of the signal cable 92 is inserted into the insertion unit 14, the operation unit 12, the universal cable 16, and the cable 24 of FIG. 1, extends up to the electrical connector 26, and is connected to the processor unit 28. Accordingly, an observation image, which is input from the observation window 62 of FIG. 2, is formed on the light-receiving surface of the imaging element 88 through the observation optical system 65 disposed in the mounting hole 68 of FIG. 3 and the prism 86 disposed in the opening portion 84, and is converted into electrical signals by the imaging element 88. Then, the electrical signals are output to the processor unit 28 through the signal cable 92 and are converted into video signals. Accordingly, the observation image is displayed on a monitor 94 that is connected to the processor unit 28. A charge coupled device (CCD) image sensor or a complementary metal oxide semiconductor (CMOS) image sensor can be used as the imaging element 88.

Figure 7:
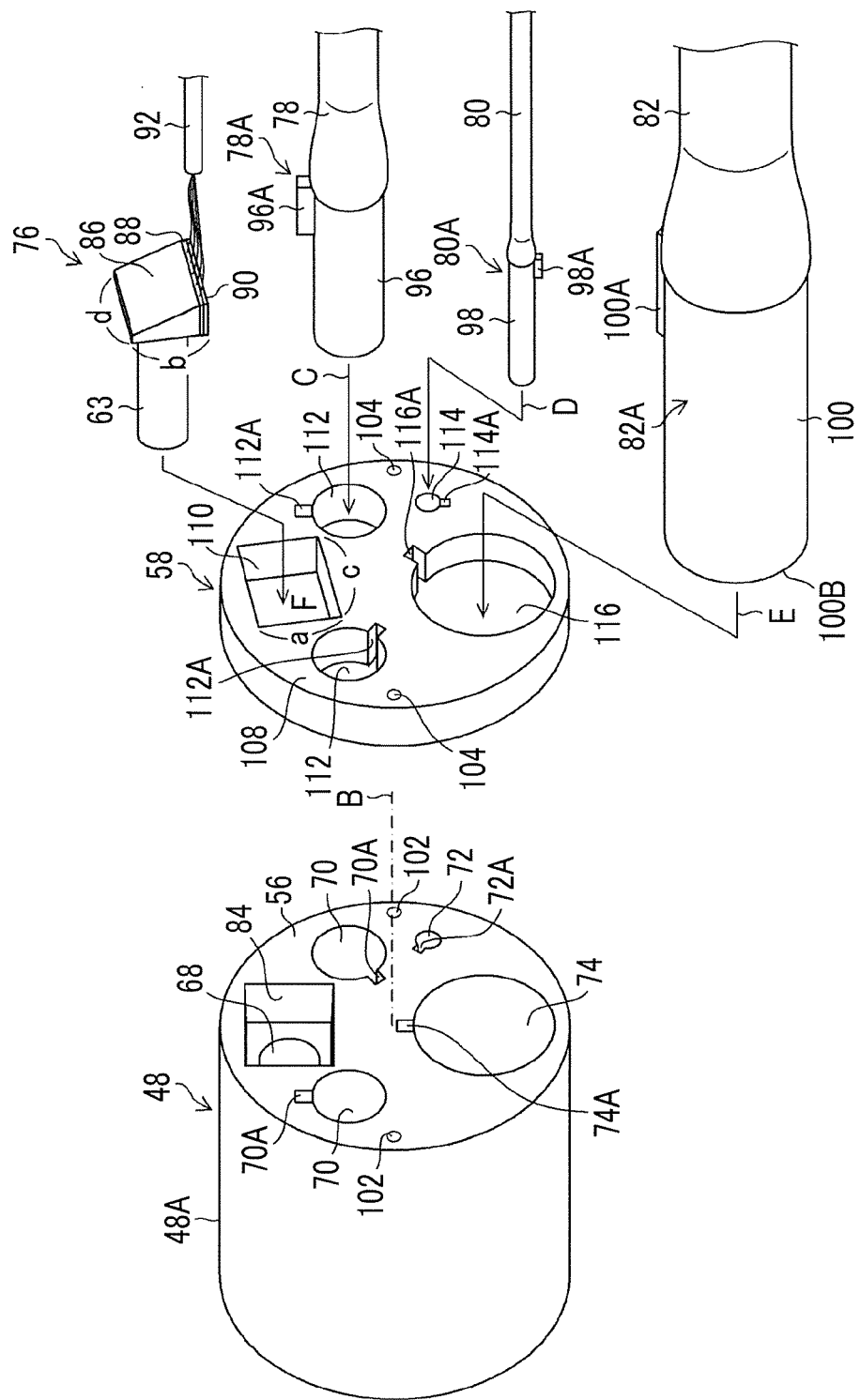
FIG. 7 is an exploded perspective view of the tip portion body and the pressing member.
Figure 8:
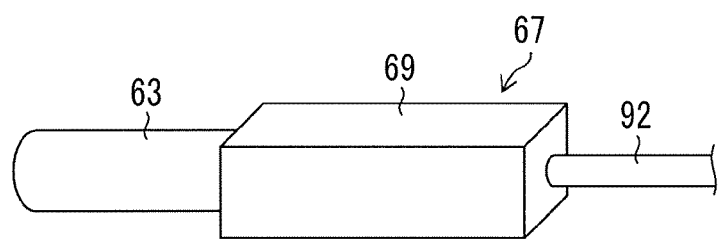
FIG. 8 is a perspective view showing another form of an imaging unit.

The form of the imaging unit is not limited to the imaging unit 76 shown in FIG. 7. For example, a form in which a case 69 by which an imaging element (not shown) is held is directly connected to the lens barrel 63 and the imaging element is disposed on the optical axis of the observation optical system 65 (see FIG. 3) held by the lens barrel 63 as in a perspective view of another imaging unit 67 shown in FIG. 8 can also be applied.

Further, the imaging unit 76 is exemplified as a member for transmitting the observation image in the embodiment, but the member for transmitting the observation image is not limited to the imaging unit 76 and an image guide member 77 (see FIG. 12), which is one of the insertion members, may be used as the member for transmitting the observation image. The image guide member 77 is an optical transmission member having a structure in which fiber bundles are inserted into a tube.

As in FIG. 5, a first groove portion 70A of which a tip protrudes from the inner peripheral surface of the mounting hole 70 is provided on each of the inner peripheral surfaces of the pair of mounting holes 70 and 70. The first groove portion 70A has a shape corresponding to a protrusion portion 96A that is provided on the tip portion 78A of each light guide member 78 (see FIG. 7). The protrusion portion 96A protrudes outward from the outer periphery of the tip portion 78A of the light guide member 78 in a radial direction. The light guide member 78 is an optical transmission member having a structure in which a single fiber or fiber bundles are inserted into a tube.

In the embodiment, the protrusion portion 96A is provided on a mouthpiece 96 that is mounted on the tip portion 78A of the light guide member 78. The protrusion portion 96A may be directly provided on the tip portion of the tube of the light guide member 78. Further, the cross-sectional shape of the protrusion portion 96A in a direction orthogonal to the central axis B is a rectangular parallelepiped shape, and the first groove portion 70A is a groove portion of which the cross-sectional shape in the direction orthogonal to the central axis B is a rectangular shape and which receives the protrusion portion 96A. The shapes of the first groove portion 70A and the protrusion portion 96A are not limited to the shapes of the embodiment.

A base end portion of the light guide member 78 is inserted into the insertion unit 14, the operation unit 12, and the universal cable 16 of FIG. 1, and extends up to the light guide connector 18. Accordingly, in a case in which the light guide connector 18 is connected to the light source device 20, illumination light emitted from the light source device 20 is transmitted to the illumination windows 22 and 22 of FIG. 2 through the light guide members 78 and is emitted forward from the illumination windows 22 and 22.

As in FIG. 5, a first groove portion 72A of which a tip protrudes from the inner peripheral surface of the mounting hole 72 is provided on the inner peripheral surface of the mounting hole 72. The first groove portion 72A has a shape corresponding to a protrusion portion 98A that is provided on the tip portion 80A of the air/water supply tube member 80 (see FIG. 7). The protrusion portion 98A protrudes outward from the outer periphery of the tip portion 80A of the air/water supply tube member 80 in the radial direction.

In the embodiment, the protrusion portion 98A has been provided on a mouthpiece 98 that is mounted on the tip portion 80A of the air/water supply tube member 80. However, the protrusion portion 98A may be directly provided on the tip portion of the air/water supply tube member 80. Further, the cross-sectional shape of the protrusion portion 98A in the direction orthogonal to the central axis B is a rectangular parallelepiped shape, and the first groove portion 72A is a groove portion of which the cross-sectional shape in the direction orthogonal to the central axis B is a rectangular shape and which receives the protrusion portion 98A. The shapes of the first groove portion 72A and the protrusion portion 98A are not limited to the shapes of the embodiment.

A base end portion of the air/water supply tube member 80 is inserted into the insertion unit 14 of FIG. 1 and communicates with an air/water supply valve (not shown) that is to be operated by the air/water supply button 30. Further, the air/water supply valve is connected to a water supply connector 99, which is provided in the light guide connector 18, through a tube (not shown). Since air/water supply means (not shown) is connected to the water supply connector 99, air and water are supplied to the water supply connector 99 from the air/water supply means. Accordingly, air or water can be sprayed to the observation window 62 from the air/water supply nozzle 64 of FIG. 2 through the operation of the air/water supply button 30.

As in FIG. 5, a first groove portion 74A of which a tip protrudes from the inner peripheral surface of the mounting hole 74 is provided on the inner peripheral surface of the mounting hole 74. The first groove portion 74A has a shape corresponding to a protrusion portion 100A that is provided on the tip portion 82A of the forceps tube member 82 (see FIG. 7). The protrusion portion 100A protrudes outward from the outer periphery of the tip portion 82A of the forceps tube member 82 in the radial direction.

In the embodiment, the protrusion portion 100A is provided on a mouthpiece 100 that is mounted on the tip portion 82A of the forceps tube member 82. However, the protrusion portion 100A may be directly provided on the tip portion of the forceps tube member 82. Further, the cross-sectional shape of the protrusion portion 100A in the direction orthogonal to the central axis B is a rectangular parallelepiped shape, and the first groove portion 74A is a groove portion of which the cross-sectional shape in the direction orthogonal to the central axis B is a rectangular shape and which receives the protrusion portion 100A. However, the shapes of the first groove portion 74A and the protrusion portion 100A are not limited to the shapes of the embodiment.

In a case in which the protrusion portion 100A is inserted into the first groove portion 74A as in FIG. 3, a tip surface 101A of the protrusion portion 100A is in contact with a stopper surface 74B that is formed on the tip side of the first groove portion 74A and is orthogonal to the central axis B. Accordingly, the movement of the mouthpiece 100 to the tip side in the direction of the central axis B is restricted. The movement of the mouthpiece 100 may be restricted in a case in which the tip surface 100B of the mouthpiece 100 is in contact with a stopper surface 75 that is formed on the tip side of the mounting hole 74 and is orthogonal to the central axis B. A structure for restricting the movement of the mouthpiece 100, which includes the tip surfaces 101A and 100B and the stopper surfaces 74B and 75, is applied to the other mouthpieces 96 and 98, the other mounting holes 70 and 72, and the other first groove portions 70A and 72A.

A method of forming the first groove portions 70A, 72A, and 74A is not particularly limited. For example, the first groove portions 70A, 72A, and 74A may be formed by cutting using a cutting tool, and the first groove portions 70A, 72A, and 74A may be formed by metal powder injection molding. Further, the tip portion body 48 can be formed by cast molding or metal powder injection molding.

A base end portion of the forceps tube member 82 is inserted into the insertion unit 14 of FIG. 1 and communicates with the forceps insertion portion 40. Accordingly, when various treatment tools 41 (see FIG. 3), such as forceps and a high-frequency knife, are inserted from the forceps insertion portion 40, the treatment tools 41 can be led to the outside from the forceps port 66 of FIG. 2. Furthermore, the forceps tube member 82 of FIG. 7 is branched and connected to a suction tube (not shown) and communicates with a suction valve (not shown) to be operated by the suction button 32 of FIG. 1. Moreover, the suction valve is connected to a suction connector 101, which is provided in the light guide connector 18, through a tube (not shown). Accordingly, when a suction pump (not shown) is connected to the suction connector 101 and the suction valve is operated by the suction button 32, residues, dirt, and the like can be drawn from the forceps port 66 through the forceps tube member 82.

As in FIG. 5, the base end face 56 of the tip portion body 48 is provided with screw holes 102 and 102. Screw members 106 (see FIG. 10), which are used to fix the pressing member 58 (see FIG. 7) to the base end face 56 of the tip portion body 48, are threadedly inserted into the screw holes 102. The screw holes 102 and 102 are provided at positions that are present on both sides of the central axis B. The screw hole 102 may be provided at only one position where the mounting holes 68, 70, 72, and 74 are not formed.

Figure 6:
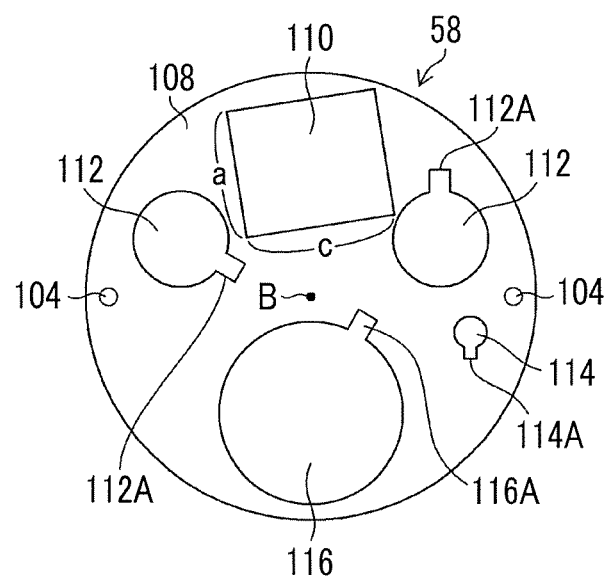
FIG. 6 is a front view of a base end face of a pressing member.

FIG. 6 is a front view of a base end face 108 of the pressing member 58. FIG. 7 is an exploded perspective view of the tip portion body 48 and the pressing member 58.

The pressing member 58 is provided with insertion holes 110, 112, 114, and 116 corresponding to the mounting holes 68, 70, 72, and 74 of the tip portion body 48 of FIG. 5.

The insertion hole 110 is a rectangular opening portion which is disposed so as to face the opening portion 84 of the tip portion body 48 and into which the imaging unit 76 can be inserted. The short side a of the insertion hole 110 is slightly longer than the short side b (see FIG. 7) of the shape of the imaging unit 76 in front view, and the long side c of the insertion hole 110 is slightly longer than the long side d of the shape of the imaging unit 76 in front view. Further, the insertion hole 110 is formed so that the short side a and the long side c are inclined with respect to the short side b and the long side d by a predetermined angle in a case in which the pressing member 58 is fixed to the base end face 56 of the tip portion body 48. Accordingly, since the substrate 90 is in contact with the tip surface 57 of the pressing member 58 in a state in which the pressing member 58 is fixed to the base end face 56 of the tip portion body 48 after the imaging unit 76 is received in the opening portion 84, the movement of the imaging unit 76 to the base end side of the insertion unit 14 is restricted. Therefore, the imaging unit 76 is fixed to the tip portion body 48 without being separated from the tip portion body 48.

Each of the insertion holes 112 is an opening portion which is disposed so as to face the mounting hole 70 and into which the tip portion 78A of the light guide member 78 can be inserted. A second groove portion 112A, which has a shape corresponding to the protrusion portion 96A, is formed at each of the insertion holes 112.

The second groove portion 112A is disposed at a second circumferential position, which is different from a circumferential position at which the first groove portion 70A is formed as a first circumferential position, in a circumferential direction around an axial direction C of the light guide member 78. Accordingly, the second groove portion 112A is disposed at a position that does not overlap the first groove portion 70A in a case in which the base end face 108 of the pressing member 58 is seen from the base end side.

Therefore, since the protrusion portion 96A is in contact with the tip surface 57 of the pressing member 58 in a state in which the pressing member 58 is fixed to the base end face 56 of the tip portion body 48 after the tip portion 78A of the light guide member 78 is mounted in the mounting hole 70 and the protrusion portion 96A is mounted in the first groove portion 70A, the movement of the light guide member 78 to the base end side of the insertion unit 14 is restricted. Accordingly, the light guide member 78 is fixed to the tip portion body 48 without being separated from the tip portion body 48.

The insertion hole 114 is an opening portion which is disposed so as to face the mounting hole 72 and into which the tip portion 80A of the air/water supply tube member 80 can be inserted. A second groove portion 114A, which has a shape corresponding to the protrusion portion 98A, is formed at the insertion hole 114.

The second groove portion 114A is disposed at a second circumferential position, which is different from a circumferential position at which the first groove portion 72A is formed as a first circumferential position, in a circumferential direction around an axial direction D of the air/water supply tube member 80. Accordingly, the second groove portion 114A is disposed at a position that does not overlap the first groove portion 72A in a case in which the base end face 108 of the pressing member 58 is seen from the base end side.

Therefore, since the protrusion portion 98A is in contact with the tip surface 57 of the pressing member 58 in a state in which the pressing member 58 is fixed to the base end face 56 of the tip portion body 48 after the tip portion 80A of the air/water supply tube member 80 is mounted in the mounting hole 72 and the protrusion portion 98A is mounted in the first groove portion 72A, the movement of the air/water supply tube member 80 to the base end side of the insertion unit 14 is restricted. Accordingly, the air/water supply tube member 80 is fixed to the tip portion body 48 without being separated from the tip portion body 48.

The insertion hole 116 is an opening portion which is disposed so as to face the mounting hole 74 and into which the tip portion 82A of the forceps tube member 82 can be inserted. A second groove portion 116A, which has a shape corresponding to the protrusion portion 100A, is formed at the insertion hole 116.

The second groove portion 116A is disposed at a second circumferential position, which is different from a circumferential position at which the first groove portion 74A is formed as a first circumferential position, in a circumferential direction around an axial direction E of the forceps tube member 82. Accordingly, the second groove portion 116A is disposed at a position that does not overlap the first groove portion 74A in a case in which the base end face 108 of the pressing member 58 is seen from the base end side.

Therefore, since the protrusion portion 100A is in contact with the tip surface 57 of the pressing member 58 in a state in which the pressing member 58 is fixed to the base end face 56 of the tip portion body 48 after the tip portion 82A of the forceps tube member 82 is mounted in the mounting hole 74 and the protrusion portion 100A is mounted in the first groove portion 74A, the movement of the forceps tube member 82 to the base end side of the insertion unit 14 is restricted. Accordingly, the forceps tube member 82 is fixed to the tip portion body 48 without being separated from the tip portion body 48.

A method of forming the second groove portions 112A, 114A, and 116A is not particularly limited. For example, the second groove portions 112A, 114A, and 116A may be formed by cutting using a cutting tool, and the second groove portions 112A, 114A, and 116A may be formed by metal powder injection molding. In a case in which the pressing member 58 is made of a resin, the pressing member 58 may be formed by cutting, injection molding, or the like.

Further, the pressing member 58 is provided with through holes 104 and 104. Since each of the through holes 104 is formed so as to face the screw hole 102, a screw member 106 (see FIG. 10) is inserted from each through hole 104 and is threadedly inserted into each screw hole 102. Accordingly, the pressing member 58 is fixed to the base end face 56 of the tip portion body 48. Since the screw holes 102 are formed along the central axis B, the screw holes 102 do not affect the outer diameter of the tip portion body 48.

Other members may be used instead of the screw members 106 to fix the pressing member 58 to the tip portion body 48, but the pressing member 58 can be easily attached to/detached from the tip portion body 48 since the screw members 106 are used. Accordingly, the pressing member 58 can be easily detached from the tip portion body 48 in a case in which the insertion members are repaired or replaced.

Figure 12:
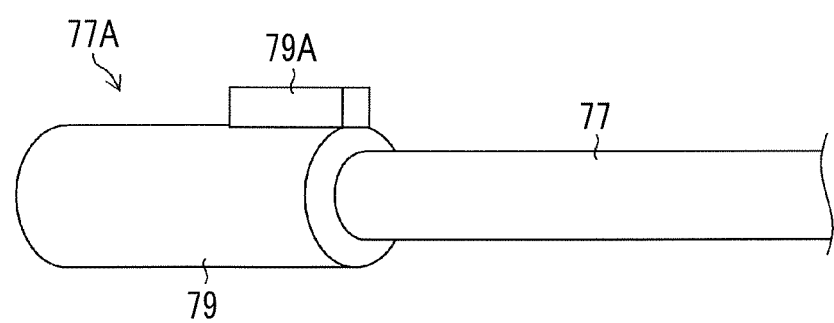
FIG. 12 is a perspective view of a tip portion of an image guide member.

In a case in which an image guide member 77 shown in FIG. 12 is used instead of the imaging unit 76, a protrusion portion 79A is provided on a lens barrel 79 of a tip portion 77A of the image guide member 77. Further, a mounting hole in which the tip portion 77A of the image guide member 77 is to be mounted and a first groove portion in which the protrusion portion 79A is to be mounted are provided in the tip portion body 48 shown in FIG. 5. Furthermore, an insertion hole into which the tip portion 77A of the image guide member 77 is to be inserted and a second groove portion into which the protrusion portion 79A is inserted may be provided in the pressing member 58. Accordingly, since the protrusion portion 79A is in contact with the tip surface 57 of the pressing member 58, the movement of the image guide member 77 to the base end side of the insertion unit 14 is restricted. Therefore, the image guide member 77 is fixed to the tip portion body 48 without being separated from the tip portion body 48.

In the following description, there are also cases in which the light guide member 78, the air/water supply tube member 80, and the forceps tube member 82 are referred to as "insertion members", the protrusion portions 96A, 98A, and 100A are referred to as "protrusion portions", the mounting holes 70, 72, and 74 are referred to as "mounting holes", the first groove portions 70A, 72A, and 74A are referred to as "first groove portions", the insertion holes 112, 114, and 116 are referred to as "insertion holes", and the second groove portions 112A, 114A, and 116A are referred to as "second groove portions".

[First Method of Assembling Endoscope 10]

Next, a first method of assembling the endoscope 10, that is, an example of a method of assembling the imaging unit 76, the light guide members 78, the air/water supply tube member 80, and the forceps tube member 82 to the tip portion body 48 will be described with reference to FIGS. 7 to 11.

Figure 9:
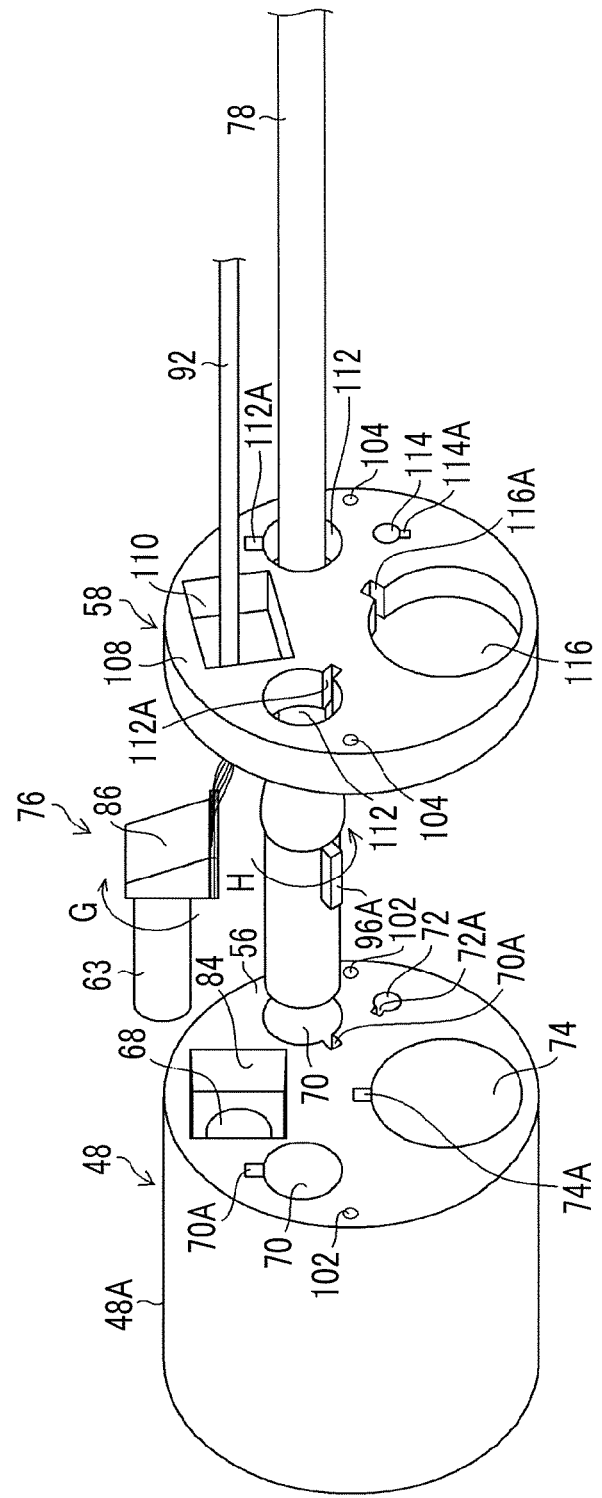
FIG. 9 is a view showing a method of assembling the imaging unit and a light guide member to the tip portion body.
Figure 10:
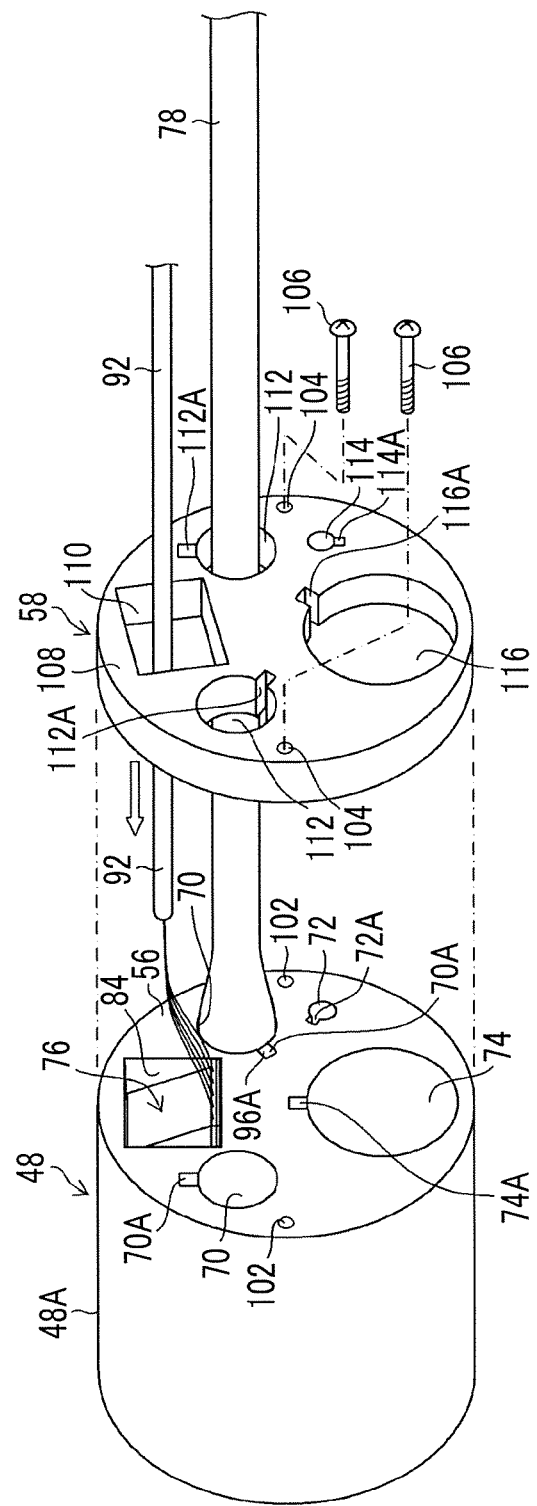
FIG. 10 is a view showing that the imaging unit and the tip portion of each light guide member are mounted on the tip portion body.
Figure 11:
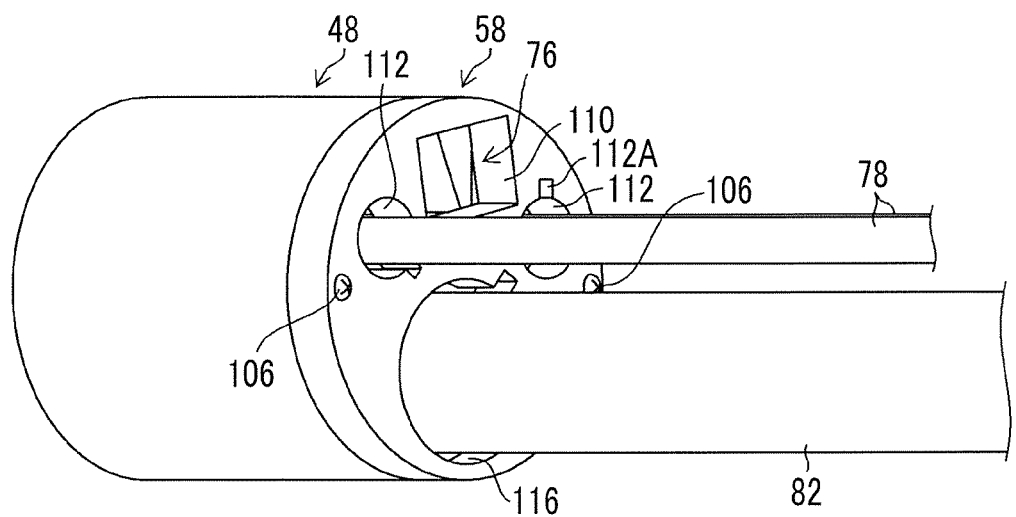
FIG. 11 is a view showing that the imaging unit, the light guide members, an air/water supply tube member, and a forceps tube member are fixed to the tip portion body.

FIG. 9 is a view showing a method of assembling the imaging unit 76 and the light guide member 78 to the tip portion body 48, FIG. 10 is a view showing that the imaging unit 76 and the tip portion of each light guide member 78 are mounted on the tip portion body 48, and FIG. 11 is a view showing that the imaging unit 76, the light guide members 78, the air/water supply tube member 80 (not shown), and the forceps tube member 82 are fixed to the tip portion body 48.

Figure 13:
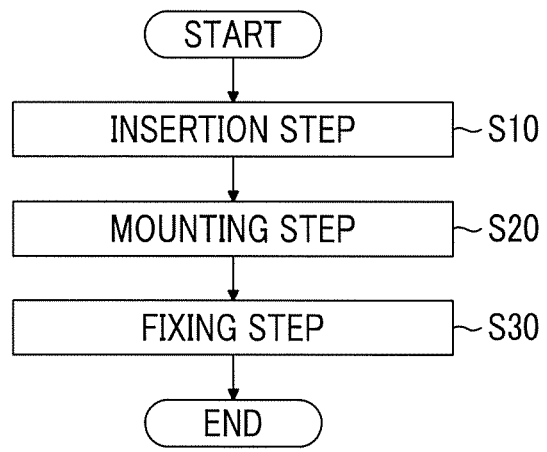
FIG. 13 is a flowchart illustrating a method of assembling the endoscope.

FIG. 13 is a flowchart illustrating a method of assembling the endoscope 10 of the embodiment. According to FIG. 13, the method of assembling the endoscope 10 of the embodiment includes an insertion step (S(Step)10) of inserting the tip portion of the insertion member into the insertion hole of the pressing member in a state in which the circumferential position of the protrusion portion and the circumferential position of the second groove portion are aligned with each other, a mounting step (S20) of mounting the tip portion of the insertion member in the mounting hole of the tip portion body in a state in which the circumferential position of the protrusion portion and the circumferential position of the first groove portion are aligned with each other after the insertion step (S10), and a fixing step (S30) of fixing the pressing member to the tip portion body. The method will be specifically described below.

First, the imaging unit 76 is inserted into the tip portion body 48 through the insertion hole 110 of the pressing member 58 as shown by an arrow F in FIG. 7. Then, the attitude of the imaging unit 76 is changed as shown by an arrow G in FIG. 9 and the imaging unit 76 is mounted in the opening portion 84 of the tip portion body 48 as in FIG. 10.

Next, the circumferential position of the protrusion portion 96A of the light guide member 78 is aligned with the position of the second groove portion 112A of the pressing member 58 as shown in FIG. 7 and the tip portion 78A of the light guide member 78 is inserted into the insertion hole 112 as in FIG. 9 (the insertion step of FIG. 13). After that, the light guide member 78 is rotated as shown by an arrow H to align the circumferential position of the protrusion portion 96A of the light guide member 78 with the position of the first groove portion 70A of the mounting hole 70, and the tip portion 78A of the light guide member 78 is mounted in the mounting hole 70 of the tip portion body 48 as in FIG. 10. In this case, the protrusion portion 96A is mounted in the first groove portion 70A (the mounting step of FIG. 13). Here, the cross-sectional shape of the mouthpiece 96 of the light guide member 78 is a circular shape, but a mouthpiece of which the cross-section is an elliptical shape over the entire length of the mouthpiece 96 in the axial direction may be used and a mouthpiece of which the cross-sectional shape on the tip side is a circular shape and the cross-sectional shape on the base end side is an elliptical shape may also be used.

Although not shown, the air/water supply tube member 80 and the forceps tube member 82 are mounted in the mounting holes 72 and 74 of the tip portion body 48 with the same procedure as the light guide member 78.

After that, as shown in FIG. 11, the screw members 106 are inserted into the through holes 104 of the pressing member 58, are threadedly inserted into the screw holes 102 of the tip portion body 48, and fix the pressing member 58 to the base end face 56 of the tip portion body 48 (the fixing step in FIG. 13). Accordingly, since the substrate 90 is in contact with the tip surface 57 of the pressing member 58, the movement of the imaging unit 76 to the base end side of the insertion unit 14 is restricted. Therefore, the imaging unit 76 is fixed to the tip portion body 48 without being separated from the tip portion body 48.

Further, since the protrusion portions 96A, 98A, and 100A are in contact with the tip surface 57 of the pressing member 58, the movement of the light guide members 78, the air/water supply tube member 80, and the forceps tube member 82 to the base end side of the insertion unit 14 is restricted. Accordingly, the light guide members 78, the air/water supply tube member 80, and the forceps tube member 82 are fixed to the tip portion body 48 without being separated from the tip portion body 48. Therefore, according to the endoscope 10 of the embodiment, screw holes disclosed in JP1999-56756A (JP-H11-56756A) and JP2004-290492A do not need to be provided in the tip portion body, that is, the diameter of the insertion unit 14 of the endoscope 10 does not need to be increased and the tip portions 78A, 80A, and 82A of the light guide members 78, the air/water supply tube member 80, and the forceps tube member 82 can be fixed to the tip portion body 48.

According to the endoscope 10 of the embodiment, the protrusion portion is provided on the tip portion of the insertion member, the first groove portion is provided at the mounting hole of the tip portion body 48, the second groove portion is provided at the insertion hole of the pressing member 58, and the second groove portion is disposed at the second circumferential position that is different from the first circumferential position in the circumferential direction around the axial direction of the insertion member. Accordingly, since the protrusion portion is in contact with the tip surface 57 of the pressing member 58, the movement of the insertion member to the base end side of the insertion unit 14 is restricted. Therefore, the insertion member is fixed to the tip portion body 48 without being separated from the tip portion body 48. Accordingly, since the screw holes disclosed in JP1999-56756A (JP-H11-56756A) and JP2004-290492A do not need to be provided in the tip portion body of the endoscope 10 of the embodiment, the tip portion of the insertion member can be fixed to the tip portion body 48 without an increase in the diameter of the insertion unit 14 of the endoscope 10.

Further, it is preferable that the first groove portion 70A of at least one mounting hole 70 (the right mounting hole 70 in FIG. 5) of the mounting holes 70, 72, and 74 is formed toward the central axis B in a plane orthogonal to the central axis B as in FIG. 5. That is, the first groove portion 70A is provided so as to avoid interfering with the other mounting holes 72 and 74 or the first groove portions 72A and 74A. However, since the first groove portion 70A is formed so that a direction in which the first groove portion 70A protrudes from the inner peripheral surface of the mounting hole 70 is directed to the central axis B, an increase in the diameter of the tip portion body 48 caused by the first groove portion, which is formed so as to be separated from the central axis B, can be prevented. Further, it is possible to reduce the diameter of the tip portion body 48 by forming all the first groove portions toward the central axis B.

Furthermore, since the mouthpiece mounted on the tip portion of the insertion member is provided and the protrusion portion is provided on the mouthpiece, the protrusion portion can be easily disposed on the tip portion of the insertion member.

[Another Structure for Fixing Insertion Member to Tip Portion Body 48]

Figure 14:
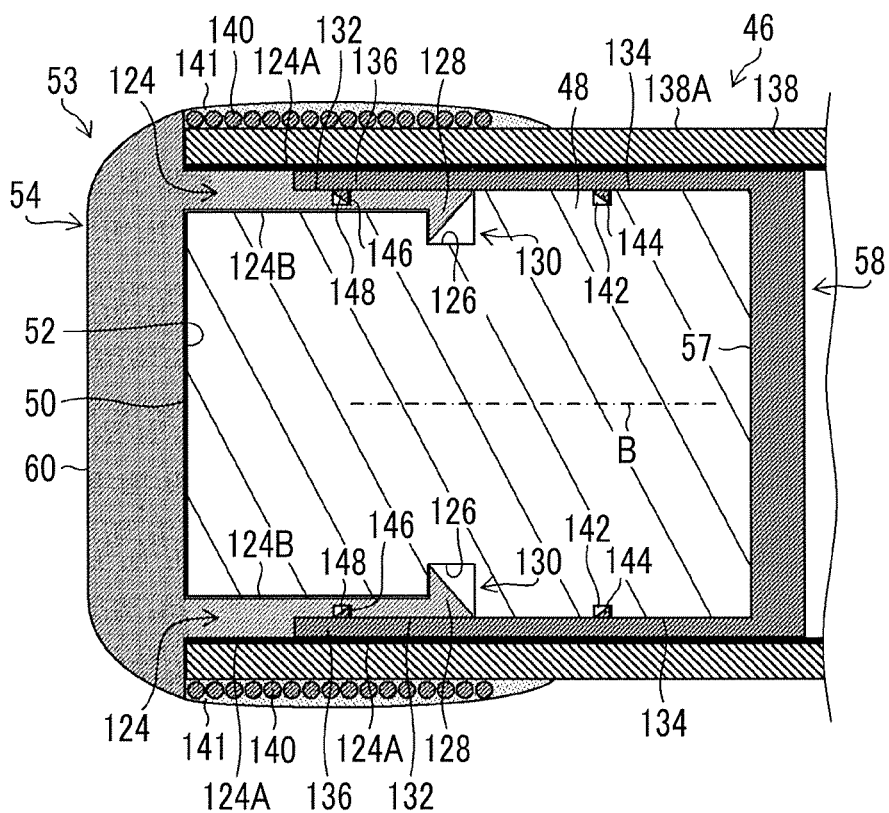
FIG. 14 is a cross-sectional view of a hard tip part.
Figure 15:
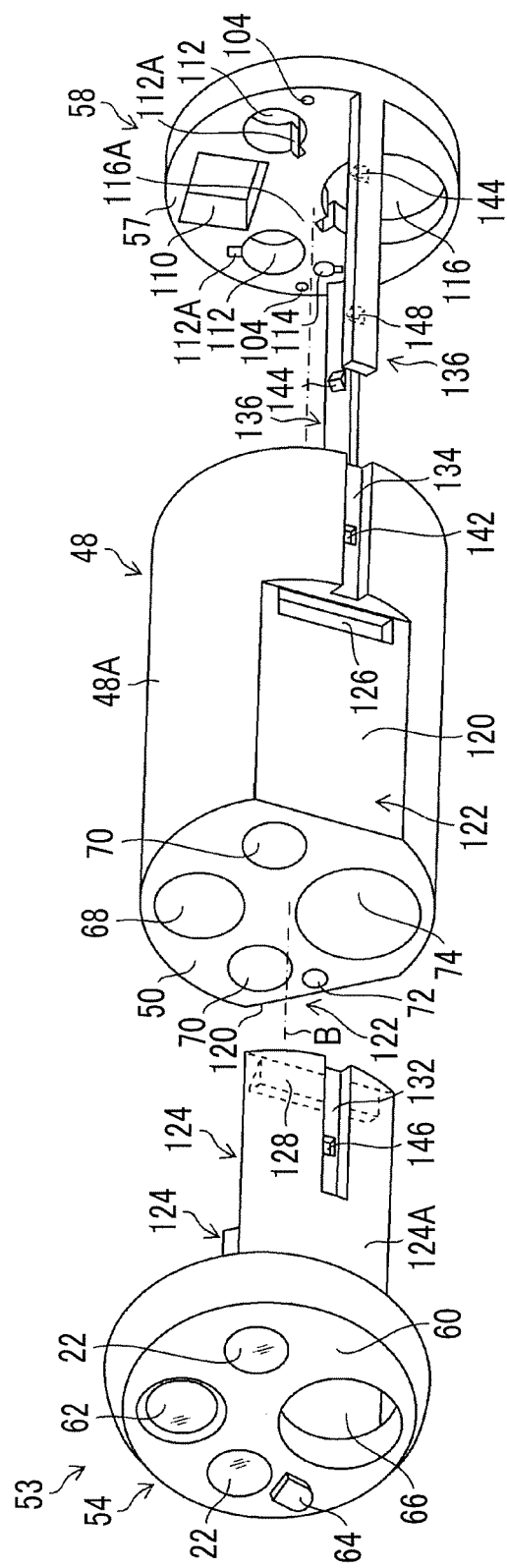
FIG. 15 is an exploded perspective view of the hard tip part shown in FIG. 14.
Figure 16:
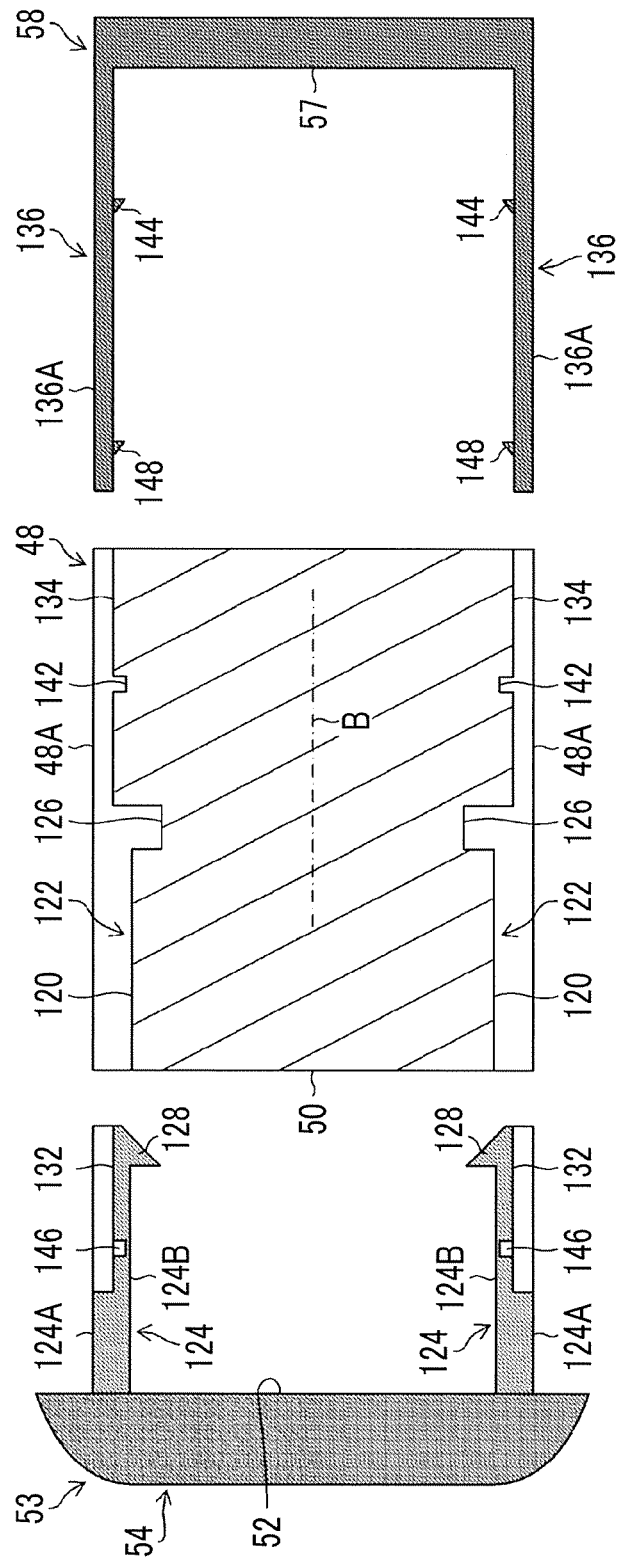
FIG. 16 is a cross-sectional view of the hard tip part shown in FIG. 15.

FIGS. 14 to 16 are views showing another structure for fixing an insertion member to a tip portion body 48. That is, FIG. 14 is a cross-sectional view of a hard tip part 46, FIG. 15 is an exploded perspective view of the hard tip part 46, and FIG. 16 is a cross-sectional view of FIG. 15. The same members as the members shown in FIGS. 1 to 11 or members similar to the members shown in FIGS. 1 to 11 are denoted by the same reference numerals as the reference numerals shown in FIGS. 1 to 11.

Another fixing structure shown in FIGS. 14 to 16 is a structure that does not use the screw members 106 shown in FIG. 10 and uses a pair of mounting portions 122 of a tip portion body 48, a pair of cap body-side extending portions 124 of a cap 53, and a pair of pressing member-side extending portions 136 of a pressing member 58 to fix an insertion member to the tip portion body 48.

The hard tip part 46 includes the tip portion body 48, the cap 53, and the pressing member 58.

The cap 53 includes a plate-like cap body 54 including a base end face 52 that faces a tip surface 50 of the tip portion body 48 and is in contact with the tip surface 50.

The tip portion body 48 includes a pair of mounting portions 122 including mounting surfaces 120 that are a part, which is formed in a planar shape, of an outer peripheral surface 48A of the tip portion body 48. A method of forming the mounting surface 120 is not particularly limited. For example, the outer peripheral surface 48A of the tip portion body 48 may be cut by a cutting tool to form the mounting surface 120, and the mounting surface 120 may be formed by cast molding.

Further, the cap 53 includes a pair of cap body-side extending portions 124 that extends toward the tip portion body 48 from a base end face 52 of the cap body 54. The cap body-side extending portion 124 includes an outer surface 124A and a contact surface 124B that is provided closer to a central axis B than the outer surface 124A and is in contact with the mounting surface 120.

Furthermore, a first engagement portion 126 is formed on each mounting surface 120 of the tip portion body 48, and a second engagement portion 128 is formed on the contact surface 124B of each cap body-side extending portion 124. The hard tip part 46 is provided with connecting portions 130 (see FIG. 14) that connect the cap 53 to the tip portion body 48 through an engagement between the first and second engagement portions 126 and 128.

Moreover, a first recessed fitting portion 132 is formed along the central axis B on the outer surface 124A of each cap body-side extending portion 124. Further, a pair of second recessed fitting portions 134, which is to be connected to the first recessed fitting portions 132, is formed along the central axis B on the outer peripheral surface 48A of the tip portion body 48. In addition, a pair of pressing member-side extending portions 136, which is to be fitted into the first and second recessed fitting portions 132 and 134, is provided on a tip surface 57 of the pressing member 58 so as to extend toward the tip portion body 48.

[Second Method of Assembling Endoscope 10]

Since a procedure for mounting the imaging unit 76, the light guide members 78, the air/water supply tube member 80, and the forceps tube member 82 on the tip portion body 48 is the same as that of the first method of assembling the endoscope 10 shown in FIGS. 7 to 11, the description thereof will be omitted here and a fixing step of fixing the pressing member 58 to the tip portion body 48 will be described here.

First, the second engagement portions 128 of the cap body-side extending portions 124 are engaged with the first engagement portions 126 of the tip portion body 48, so that the cap 53 is fixed to the tip portion body 48.

Next, it is possible to fix the pressing member 58 to the base end side of the tip portion body 48 by fitting the pair of pressing member-side extending portions 136 of the pressing member 58 into the first recessed fitting portions 132 of the cap body-side extending portions 124 and the second recessed fitting portions 134 of the tip portion body 48.

In this fixing structure, empty spaces are formed on the outer peripheral surface 48A of the tip portion body 48 by the formation of the mounting portions 122 on the outer peripheral surface 48A of the tip portion body 48 and the cap body-side extending portions 124 are disposed in the spaces to fix the cap 53 to the tip portion body 48. Accordingly, the cap 53 can be fixed to the tip portion body 48 without an increase in the diameter of the tip portion body 48.

Further, the first recessed fitting portions 132 are formed on the cap body-side extending portions 124 and the second recessed fitting portions 134 are formed on the tip portion body 48. Accordingly, empty spaces of the cap body-side extending portions 124 and the tip portion body 48 are used and the pressing member-side extending portions 136 are disposed in the spaces to fix the pressing member 58 to the tip portion body 48. Accordingly, the pressing member 58 can be fixed to the tip portion body 48 without an increase in the diameter of the tip portion body 48.

Furthermore, it is preferable that the first engagement portion 126 is a first recessed portion and the second engagement portion 128 is a first protruding portion. Accordingly, it is possible to prevent the cap body 54 from falling out of the tip portion body 48 while maintaining the strength of the cap body-side extending portion 124.

Moreover, it is preferable that a coating member 138 and a filamentous fixing member 140 are provided. The coating member 138 is made of rubber and covers the outer peripheral surface 48A of the tip portion body 48, the outer surfaces 124A of the cap body-side extending portions 124, and the pressing member-side extending portions 136 in a state in which the cap body 54 and the tip portion body 48 are connected to each other by the connecting portions 130 as shown in FIG. 14; and the filamentous fixing member 140 is provided on an outer peripheral surface 138A of the coating member 138, is disposed at a position where the connecting portions 130 are provided in the direction of the central axis B, and fixes the engagement between the first and second engagement portions 126 and 128. Accordingly, since the engagement between the first and second engagement portions 126 and 128 can be secured and fixed in the radial direction through the coating member 138 by the fixing member 140, the separation of the cap body 54 and the pressing member 58 from the tip portion body 48 can be reliably prevented.

The filamentous fixing member 140 is fixed to the outer peripheral surface 138A of the coating member 138 by an adhesive 141. Further, the fixing member 140 is not limited to a filamentous fixing member and may be a stringy or belt-like fixing member. Here, a filamentous member means a slender and long member like yarn, and also includes a member that can be regarded as a piece of yarn as a whole by the entanglement of a plurality of fibers or the twist of a plurality of pieces of yarn, other than a piece of single yarn. Further, a stringy member means a member corresponding to the superordinate concept of a filamentous member, and includes a flexible rod-like member and also includes an elongated hollow member, such as a tube, other than a solid member. Furthermore, a belt-like member means a substantially long plate-like member that has a long length and a thickness smaller than the width as a whole. The stringy (including filamentous) or belt-like fixing member 140 is wound around the outer peripheral surface 138A of the coating member 138.

Figure 17:
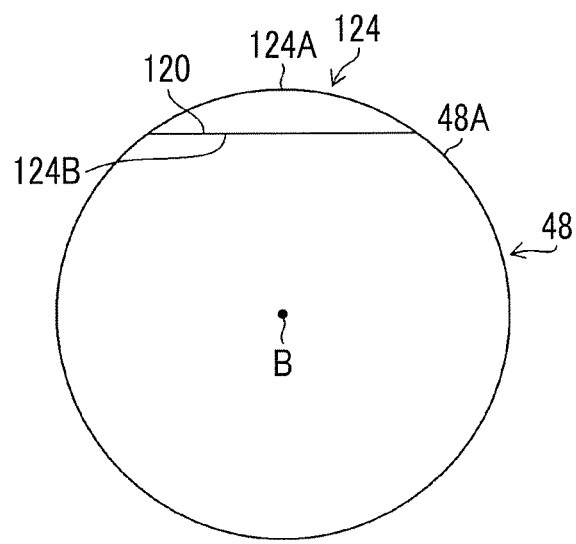
FIG. 17 is a schematic front view showing that a cap body-side extending portion is mounted on the tip portion body.

Further, as in a schematic front view of FIG. 17, the outer surface 124A of the cap body-side extending portion 124 is connected to the outer peripheral surface 48A of the tip portion body 48 so as to be flush with the outer peripheral surface 48A in a state in which the first and second engagement portions 126 and 128 are engaged with each other. That is, the outer surface 124A is formed of an arc-shaped surface that has a radius of curvature equal to the radius of curvature of the outer peripheral surface 48A, and both end portions of the arc-shaped surface are connected to the outer peripheral surface 48A. Accordingly, airtightness and watertightness between the outer peripheral surface 48A of the tip portion body 48, which includes the outer surfaces 124A of the cap body-side extending portions 124, and the coating member 138 are improved.

Furthermore, since each second recessed fitting portion 134 is provided with a second recessed portion 142 and each pressing member-side extending portion 136 is provided with a second protruding portion 144 that is to be engaged with the second recessed portion 142, it is possible to prevent the pressing member 58 from falling out of the tip portion body 48 toward the base end side while maintaining the strength of the pressing member-side extending portion 136.

Moreover, since each first recessed fitting portion 132 is provided with a third recessed portion 146 and each pressing member-side extending portion 136 is provided with a third protruding portion 148 that is to be engaged with the third recessed portion 146, it is possible to prevent the pressing member 58 from falling out of the tip portion body 48 toward the base end side while maintaining the strength of the pressing member-side extending portion 136.

Further, the pair of mounting portions 122 and the pair of cap body-side extending portions 124 are provided at positions that are present on both sides of the central axis B. Accordingly, since the cap body 54 is connected to the tip portion body 48 so as to pinch the tip portion body 48 toward the inside from the outside in the radial direction, a force for connecting the cap body 54 to the tip portion body 48 is improved. Since the pair of pressing member-side extending portions 136 is also provided at positions that are present on both sides of the central axis B likewise, the pair of pressing member-side extending portions 136 is connected to the tip portion body 48 so as to pinch the tip portion body 48 toward the inside from the outside in the radial direction. Accordingly, a force for connecting the pressing member 58 to the tip portion body 48 is improved.

Two pairs of connecting structures, which include the mounting portions 122 and the cap body-side extending portions 124, are exemplified in the embodiment, but the connecting structures are not limited thereto. For example, the connecting structures may be a pair of connecting structures and may be three or more pairs of connecting structures.

Further, in the embodiment, the falling out of the pressing member 58 from the tip portion body 48 toward the base end side is prevented since the pressing member-side extending portions 136 are secured and fixed to the cap body-side extending portions 124 in the radial direction through the coating member 138 by the fixing member 140 as in FIG. 14, and the falling out of the pressing member 58 from the tip portion body 48 toward the base end side is further prevented since the second protruding portions 144 are engaged with the second recessed portions 142 and the third protruding portions 148 are engaged with the third recessed portions 146. However, the invention is not limited thereto. For example, in the case of the premise that the pressing member-side extending portions 136 are secured and fixed to the cap body-side extending portions 124 in the radial direction through the coating member 138 by the fixing member 140, the falling out of the pressing member 58 from the tip portion body 48 toward the base end side may be prevented only by the engagement between the second recessed portions 142 and the second protruding portions 144 or only by the engagement between the third recessed portions 146 and the third protruding portion 148. Furthermore, the falling out of the pressing member 58 from the tip portion body 48 toward the base end side may be prevented only by fastening and fixing that is performed in the radial direction by the fixing member 140.

Figure 18:
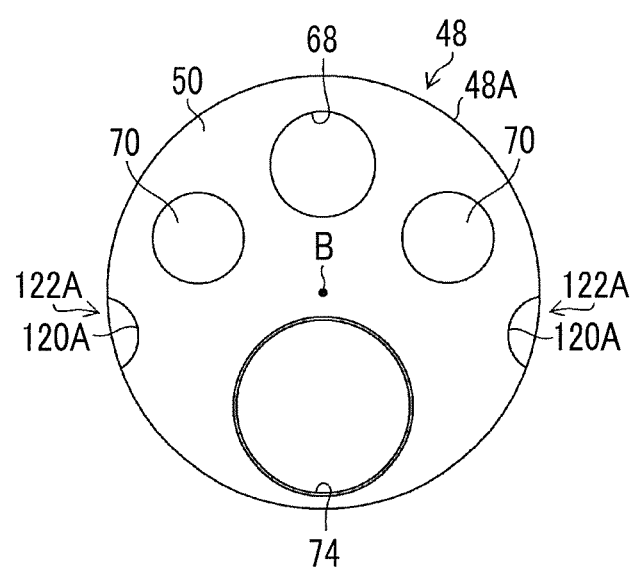
FIG. 18 is a front view of a tip portion body showing mounting portions including mounting surfaces that are a part, which is formed in a concave shape, of an outer peripheral surface of the tip portion body.

FIG. 18 is a front view of the tip portion body 48 showing mounting portions 122A including mounting surfaces 120A that are a part, which is formed in a concave shape, of the outer peripheral surface 48A of the tip portion body 48. The contact surfaces of the cap body-side extending portions 124, which are to be in contact with the concave mounting surfaces 120A, are formed as convex curved surfaces. Any shape can be applied as the shape of the mounting surface and the shape of the contact surface as long as the contact surface is in contact with the mounting surface.

EXPLANATION OF REFERENCES

A: longitudinal axis
B: central axis
10: endoscope
12: operation unit
14: insertion unit
16: universal cable
18: light guide connector
20: light source device
22: illumination window
24: cable
26: electrical connector
28: processor unit
30: air/water supply button
32: suction button
34: shutter button
36: angle knob
38: angle knob
40: forceps insertion portion
41: treatment tool
42: soft part
44: bendable part
46: hard tip part
48: tip portion body
48A: outer peripheral surface
50: tip surface
52: base end face
53: cap
54: cap body
56: base end face
57: tip surface
58: pressing member
60: tip surface
61: through hole
62: observation window
63: lens barrel
64: air/water supply nozzle
65: observation optical system
66: forceps port
67: imaging unit
68: mounting hole
69: case
70: mounting hole
70A: first groove portion
72: mounting hole
72A: first groove portion
74: mounting hole
74A: first groove portion
74B: stopper surface
75: stopper surface
76: imaging unit
77: image guide member
77A: tip portion
78: light guide member
78A: tip portion
79: lens barrel
80: air/water supply tube member
80A: tip portion
82: forceps tube member
82A: tip portion
84: opening portion
86: prism
88: imaging element 90: substrate
92: signal cable
94: monitor
96: mouthpiece
96A: protrusion portion
98: mouthpiece
98A: protrusion portion
99: water supply connector
100: mouthpiece
100A: protrusion portion
100B: tip surface
101: suction connector
101A: tip surface
102: screw hole
104: through hole
106: screw member
108: base end face
110: insertion hole
112: insertion hole
112A: second groove portion
114: insertion hole
114A: second groove portion
116: insertion hole
116A: second groove portion
120: mounting surface
120A: mounting surface
122: mounting portion
122A: mounting portion
124: cap body-side extending portion
124A: outer surface
124B: contact surface
126: first engagement portion
128: second engagement portion
130: connecting portion
132: first recessed fitting portion
134: second recessed fitting portion
136: pressing member-side extending portion
138: coating member
140: fixing member
141: adhesive
142: second recessed portion
144: second protruding portion
146: third recessed portion
148: third protruding portion

What is claimed is:

1. An endoscope comprising:
an insertion unit that has a longitudinal axis;
an insertion member that is disposed so as to be inserted into the insertion unit along the longitudinal axis of the insertion unit, wherein the insertion member is one of a light guide member, a tube member, or an image guide member;
a tip portion body that is provided close to a tip of the insertion unit and has a central axis parallel to the longitudinal axis of the insertion unit;
a disc-shaped pressing member that is in contact with a base end side of the tip portion body;
a protrusion portion that is provided on a tip portion of the insertion member and protrudes outward from an outer periphery of the tip portion of the insertion member in a radial direction;
at least one mounting hole which is provided in the tip portion body and in which the tip portion of the insertion member is inserted and mounted and a first groove portion having a shape corresponding to the protrusion portion is formed and is disposed at a first circumferential position in a circumferential direction around an axial direction of the insertion member; and
an insertion hole which is provided in the disc-shaped pressing member, into which the tip portion of the insertion member is inserted, and in which a second groove portion having a shape corresponding to the protrusion portion is formed and is disposed at a second circumferential position different from the first circumferential position in the circumferential direction around the axial direction of the insertion member,
wherein the first groove portion and the second groove portion are disposed at different locations along the longitudinal axis of the insertion unit.

2. The endoscope according to claim 1, further comprising:
a screw hole that is provided on a base end face of the tip portion body;
a screw insertion hole that is provided in the disc-shaped pressing member; and
a screw member that is inserted into the screw insertion hole and is threadedly inserted into the screw hole.

3. The endoscope according to claim 1, further comprising
a mouthpiece that is mounted on the tip portion of the insertion member,
wherein the protrusion portion is provided on the mouthpiece.

4. The endoscope according to claim 1, further comprising:
a plate-like cap body that includes a base end face facing a tip surface of the tip portion body and being in contact with the tip surface;
a mounting portion including a mounting surface that is a part, which is formed in a planar shape or a concave shape, of an outer peripheral surface of the tip portion body;
a cap body-side extending portion that extends toward the tip portion body from the base end face of the cap body and includes an outer surface and a contact surface provided closer to the central axis than the outer surface and being in contact with the mounting surface;
a connecting portion that includes a first engagement portion formed on the mounting surface and a second engagement portion formed on the contact surface and connects the cap body to the tip portion body through engagement between the first and second engagement portions;
a first recessed fitting portion that is formed along the central axis on the outer surface of the cap body-side extending portion;
a second recessed fitting portion that is formed along the central axis on the outer peripheral surface of the tip portion body and is connected to the first recessed fitting portion; and
a disc-shaped pressing member-side extending portion that is provided on a tip surface of the disc-shaped pressing member and is engaged with the first recessed fitting portion and the second recessed fitting portion.

5. The endoscope according to claim 4,
wherein the first engagement portion is a first recessed portion, and
the second engagement portion is a first protruding portion.

6. The endoscope according to claim 4, further comprising:
a coating member that covers the outer peripheral surface of the tip portion body, the outer surface of the cap body-side extending portion, and the disc-shaped pressing member-side extending portion in a case in which the cap body and the tip portion body are connected to each other by the connecting portion; and a stringy or belt-like fixing member that is provided on an outer peripheral surface of the coating member, is disposed at a position where the connecting portion is provided in a direction of the central axis, and fixes engagement between the first and second engagement portions.

7. The endoscope according to claim 4, further comprising:
   a second recessed portion that is provided on the second recessed fitting portion; and
   a second protruding portion that is provided on the disc-shaped pressing member-side extending portion and is engaged with the second recessed portion.

8. The endoscope according to claim 4, further comprising:
   a third recessed portion that is provided on the first recessed fitting portion; and
   a third protruding portion that is provided on the disc-shaped pressing member-side extending portion and is engaged with the third recessed portion.

9. The endoscope according to claim 1,
   wherein the at least one mounting hole comprises a plurality of mounting holes, and at least one of the plurality of mounting holes has the first groove portion being formed so that a direction in which the first groove portion protrudes from an inner peripheral surface of the mounting hole is directed to the central axis in a plane orthogonal to the central axis.

10. A method of assembling an endoscope, the endoscope including an insertion unit that has a longitudinal axis, an insertion member that is disposed so as to be inserted into the insertion unit along the longitudinal axis of the insertion unit, wherein the insertion member is one of a light guide member, a tube member, or an image guide member, a tip portion body that is provided close to a tip of the insertion unit, a disc-shaped pressing member that is in contact with a base end side of the tip portion body, a protrusion portion that is provided on a tip portion of the insertion member and protrudes outward from an outer periphery of the tip portion of the insertion member in a radial direction, a mounting hole which is provided in the tip portion body and in which the tip portion of the insertion member is inserted and mounted and a first groove portion having a shape corresponding to the protrusion portion is formed and is disposed at a first circumferential position in a circumferential direction around an axial direction of the insertion member, and an insertion hole which is provided in the disc-shaped pressing member, into which the tip portion of the insertion member is inserted, and in which a second groove portion having a shape corresponding to the protrusion portion is formed and is disposed at a second circumferential position different from the first circumferential position in the circumferential direction around the axial direction of the insertion member, wherein the first groove portion and the second groove portion are disposed at different locations along the longitudinal axis of the insertion unit, the method comprising:
    an insertion step of inserting the tip portion of the insertion member into the insertion hole of the disc-shaped pressing member in a state in which a circumferential position of the protrusion portion and a circumferential position of the second groove portion are aligned with each other;
    a mounting step of mounting the tip portion of the insertion member in the mounting hole of the tip portion body in a state in which the circumferential position of the protrusion portion and a circumferential position of the first groove portion are aligned with each other after the insertion step; and
    a fixing step of fixing the disc-shaped pressing member to the tip portion body.

\* \* \* \* \*